ately active iridium complexes of the formula I and mixtures of the diastereomers

United States Patent
Kaschig

Patent Number: 4,851,534
Date of Patent: Jul. 25, 1989

[54] OPTICALLY ACTIVE IRIDIUM COMPLEXES, THEIR PREPARATION AND THEIR USE IN TRANSFER HYDROGENATION

[75] Inventor: Jürgen Kaschig, Freiburg, Fed. Rep. of Germany

[73] Assignee: Ciba-Geigy Corporation, Ardsley, N.Y.

[21] Appl. No.: 47,100

[22] Filed: May 8, 1987

[30] Foreign Application Priority Data

May 16, 1986 [CH] Switzerland ............... 1986/86

[51] Int. Cl.[4] ............... C07F 15/00; C07B 53/00; B01J 31/22
[52] U.S. Cl. ............... 546/12; 502/155
[58] Field of Search ............... 546/12

[56] References Cited

PUBLICATIONS

Zassinovich, Journal of Organometallic Chem., vol. 222, pp. 323–329 (1981).
Brunner, Chem Ber., vol. 117, pp. 1330–1354 (1984).
Chalk et al, Ann. New York Acad Sci. 172, 533 (1971).

Primary Examiner—Mark L. Berch
Attorney, Agent, or Firm—Harry Falber

[57] ABSTRACT

Optically active iridium complexes of the formula I and mixtures of the diastereomers

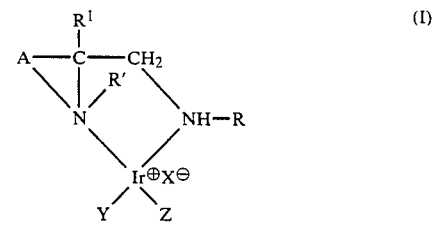

in which $R^1$ and $R'$ are H and A is a radical of the formula II, IIa or IIb

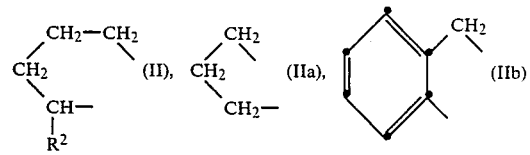

or $R^1$ and $R'$ represent a bond and A is a radical of the formula IIc

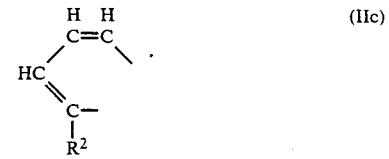

in which $R^2$ is —H or —CH$_3$, $X^\ominus$ is an anion of an inorganic or organic acid, Y and Z are each ethylene, or Y and Z together represent an open-chain or cyclic diene having 6–10 C atoms, whose double bonds are separated by one or two C atoms, and R is a hydrocarbon radical having at least one chiral C atom or a hydrocarbon radical having at least one hetero atom and at least one chiral C atom, or A is a radical of the formula II, IIa or IIb and R is phenyl, naphthyl, 2-methylphen-1-yl or 2,6-dimethylphen-1-yl. The complexes are suitable as enantioselective catalysts.

12 Claims, No Drawings

OPTICALLY ACTIVE IRIDIUM COMPLEXES, THEIR PREPARATION AND THEIR USE IN TRANSFER HYDROGENATION

The present invention relates to optically active cationic iridium(I) complexes having an asymmetric secondary amine ligand and a diene ligand, a process for their preparation, and their use as homogeneous enantioselective catalysts.

G. Zassinovich et al., in Journal of Organometallic Chemistry, 222, pages 323–329 (1981), describe cationic iridium(I) complexes having a 1,5-cyclooctadiene ligand and a 2-pyridinaldimine ligand which is substituted at the imine N atom by optically active α-phenylethyl or 3-pinanemethyl. They act as enantioselective homogeneous catalysts in the transfer hydrogenation of prochiral ketones with isopropanol. Although high yields are achieved in the reaction, the optical yield (enantiomeric excess) is relatively low.

H. Brunner et al., in Chem. Ber., 117, pages 1330–1354 (1984), describe cationic rhodium(I) complexes having a cycloocta-1,5-diene ligand and an asymmetric α-(secondary aminomethyl)-pyridine ligand as homogeneous catalysts for the enantioselective hydrosilylation of prochiral ketones.

The invention relates to optically active iridium complexes of the formula I and mixtures of the diastereomers.

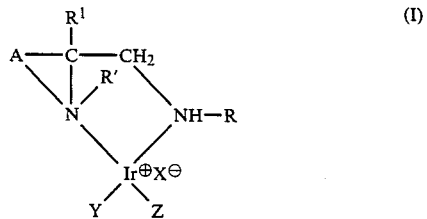

in which $R^1$ and $R'$ are H and A is a radical of the formula II, IIa or IIb

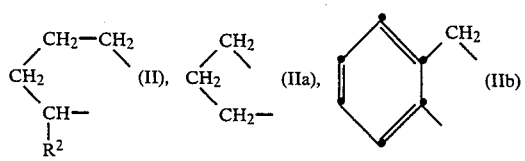

or $R^1$ and $R'$ represent a bond and A is a radical of the formula IIc

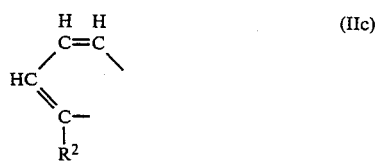

in which $R^2$ is —H or —$CH_3$, $X^-$ is an anion of an inorganic or organic acid, Y and Z are each ethylene, or Y and Z together represent an open-chain or cyclic diene having 6–10 C atoms, whose double bonds are separated by one or two C atoms; and R is a hydrocarbon radical having at least one chiral C atom or a hydrocarbon radical having at least one hetero atom and at least one chiral C atom, or A is a radical of the formula II, IIa or IIb and R is phenyl, naphthyl, 2-methylphen-1-yl or 2,6-dimethylphen-1-yl.

Optically active means that at least one chiral C atom predominantly has the S or R configuration.

$X^\ominus$ as an anion of a monobasic inorganic or organic acid can be, for example, $F^\ominus$, $Cl^\ominus$, $Br^\ominus$, $I^\ominus$, $ClO_4^\ominus$, $NO_3^\ominus$, $BrO_3^\ominus$, $HSO_4^\ominus$, $H_2PO_3^\ominus$, $H_2PO_4^\ominus$, $BF_4^\ominus$, $B(phenyl)_4^\ominus$, $PF_6^\ominus$, $SbF_6^\ominus$, $AsF_6^\ominus$, $SbCl_6^\ominus$, $SbCl_5F^\ominus$, $HCOO^\ominus$, $CH_3COO^\ominus$, $CCl_3COO^\ominus$, $CF_3COO^\ominus$, $CH_3SO_3^\ominus$, $CCl_3SO_3^\ominus$, $CF_3SO_3^\ominus$, phenyl-$SO_3^\ominus$ or p-toluyl-$SO_3^\ominus$. In a preferred embodiment, $X^\ominus$ is $BF_4^\ominus$, $ClO_4^\ominus$, $CF_3SO_3^\ominus$ or $PF_6^\ominus$.

Y and Z are each preferably ethylene, or Y and Z together are preferably a diene having 6 to 8 C atoms, whose diene groups are bonded in particular via 2 C atoms. In a preferred embodiment, Y and Z together are 1,5-cyclooctadiene, norbornadiene or 1,5-hexadiene.

A preferred subgroup of iridium complexes comprises those of the formula I, in which R is a radical of the formula III

in which $R^3$, $R^4$ and $R^5$ differ from one another when they do not contain at least 1 chiral C atom, and are a hydrogen atom, $C_1$–$C_4$-alkyl, $C_1$–$C_4$-alkoxy, cycloalkyl having 5 to 7 ring C atoms which is unsubstituted or substituted by $C_1$–$C_4$-alkyl or phenyl, cycloalkylalkyl which is unsubstituted or substituted by $C_1$–$C_4$-alkyl or phenyl and has 5 to 7 ring C atoms and 1 or 2 C atoms in the alkylene group, phenyl, naphthyl, benzyl or β-phenylethyl; or $R^4$ and $R^5$ together are $C_1$–$C_4$-alkyl-substituted or phenyl-substituted linear $C_4$- or $C_5$-alkylene, $C_4$- or $C_5$-oxaalkylene or $C_5$-dioxaalkylene having at least one chiral C atom. In a preferred embodiment, $R^3$ in formula III is a hydrogen atom.

$C_1$–$C_4$-alkyl and $C_1$–$C_4$-alkoxy radicals may be methyl, ethyl, n-propyl, isopropyl, n-butyl, isobutyl, tert-butyl and the corresponding alkoxy radicals. Alkyl radicals $R^3$, $R^4$ and $R^5$ are preferably methyl or ethyl and alkoxy radicals $R^3$, $R^4$ and $R^5$ are preferably methoxy. Cycloalkyl radicals $R^3$ to $R^5$ are preferably cyclopentyl, cycloheptyl and in particular cyclohexyl. Cycloalkylalkyl radicals $R^2$ to $R^4$ are preferably cyclohexylmethyl. $R^3$ and $R^4$ together as $C_3$–$C_4$-oxaalkylene are preferably 2-oxabutylene or 2- or 3-oxapentylene and as $C_3$-dioxaalkylene are preferably 2,4-dioxapentylene. $C_1$–$C_4$-alkyl as a substituent for $R^3$ to $R^5$ can be methyl, ethyl, n-propyl, isopropyl or butyl. Preferred substituents are methyl and phenyl.

A preferred subgroup of iridium complexes of the formula I comprises those in which, in formula III, $R^3$ is H, $R^4$ is $C_1$–$C_4$-alkyl, $C_1$–$C_4$-alkoxy or phenyl and $R^5$ is phenyl, benzyl or naphthyl, and $R^3$ and $R^4$ are not both phenyl; or $R^3$ and $R^5$ are each H and $R^4$ corresponds to the formula

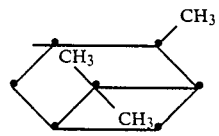

or the group —CR$^3$R$^4$R$^5$ corresponds to the formula

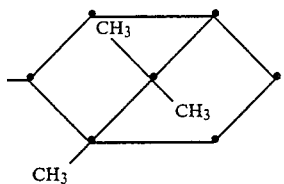

or R$^3$ is H and R$^4$ and R$^5$ together are pentamethylene which is substituted in the 2-position by C$_1$–C$_4$-alkyl, or are 2,4-dioxapentylene which is substituted in the 1- and/or 3-position by C$_1$–C$_4$-alkyl or phenyl.

Another embodiment of preferred iridium complexes comprises those in which the radical of the formula III corresponds to the radicals

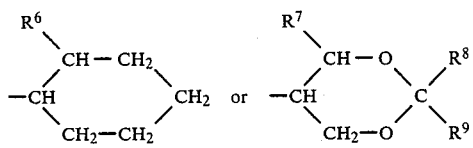

in which R$^6$ is methyl or phenyl, R$^7$ is methyl or phenyl and R$^8$ and R$^9$ are methyl, or R$^8$ is H and R$^9$ is phenyl.

Iridium complexes of the formula I, in which R$^1$ and R' are a bond and A is a radical of the formula IIc, in which R$^2$ is methyl and R corresponds to the radicals

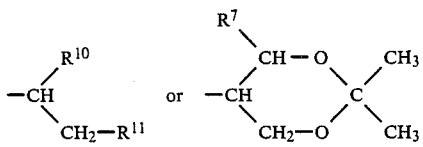

in which R$^7$ is phenyl, R$^{10}$ is phenyl or naphthyl and R$^{11}$ is H, or R$^{10}$ and R$^{11}$ are phenyl, are particularly preferred.

Another preferred subgroup comprises iridium complexes of the formula I, in which R$^1$ and R' are a bond and A is a radical of the formula IIc, in which R$^2$ is H and R is 2-methylcyclohex-1-yl, 2-phenylcyclohex-1-yl

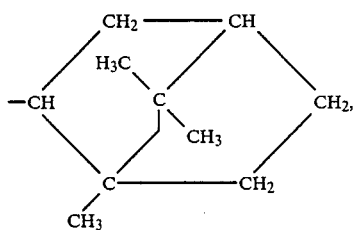

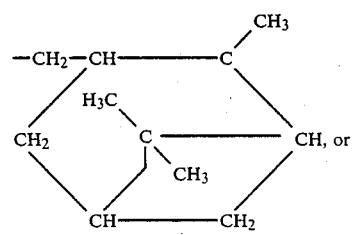

-continued

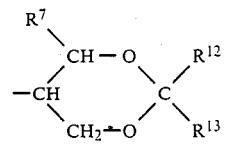

in which R$^7$ is phenyl and R$^{12}$ and R$^{13}$ are —CH$_3$, or R$^{12}$ is H and R$^{13}$ is phenyl.

In a preferred embodiment, the iridium complexes of the formula I are those in which R$^1$ and R' are H and A is a radical of the formula II and R is a radical

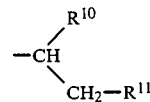

in which R$^{10}$ and R$^{11}$ are phenyl, or R$^{10}$ is phenyl or naphthyl and R$^{11}$ is H or R$^{10}$ is methyl and R$^{11}$ is phenyl.

Preferred iridium complexes of the formula I in which R$^1$ and R' are each H and A is a radical of the formula IIa are those in which R is phenyl, 2-methylphen-1-yl or 2,6-dimethylphen-1-yl.

Other preferred iridium complexes of the formula I are those in which X$^\ominus$ is BF$_4^\ominus$ and Y and Z together are 1,5-cyclooctadiene.

The iridium complexes of the formula I can be obtained by processes which are known per se [see Inorganica Chimica Acta 73 (1983), pages 275–279], by reacting [(acetonitrile)$_2$(YZ)]IrX with an optically active secondary amine of the formula IV

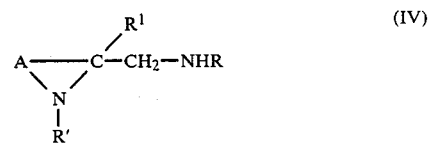

in which Y, Z, X, A, R, R$^1$ and R' have the meanings stated in claim 1. The preparation of the acetonitrile complex is likewise described there. The complexes [IrCl(YZ)]$_2$ used for the preparation of the acetonitrile complex are obtainable, for example, by the reaction of dichlorotetrakis(alkene)diiridium(I) (alkene: for example, cyclooctene) with ethylene or a diene YZ.

The reactions are carried out in general at temperatures of —10° to 30° C. in an inert solvent and in the absence of oxygen and of moisture. Examples of suitable inert solvents are hydrocarbons, such as benzene, toluene, xylene, petroleum ether, hexane, cyclohexane and methylcyclohexane; and ethers, such as, for example, diethyl ether, dibutyl ether, tetrahydrofuran and dioxane, as well as halogenated hydrocarbons, for example chloroform, methylene chloride and chlorobenzene. To prepare salts of the formula I with anions of monobasic inorganic or organic acids, the salts of the formula I can be reacted, either directly after the reaction or after isolation and purification and redissolution in polar solvents (for example alcohols, ethers or ketones, with or without the addition of water), with an alkali metal salt M$^\oplus$X'$^\ominus$ and then isolated. X'$^\ominus$ is an anion, differing from X$^\ominus$ of a monobasic inorganic or organic acid, and M$^\oplus$ is preferably sodium. The iridium complexes according to the invention are crystalline and can be isolated by filtration and purified by recrystallization. Some of the optically active secondary amines of the formula IV are known or are commercially available, or they can be prepared by known processes. Amines of the formula IV in which A is a radical of the formula IIc and $R^1$ and $R'$ are a bond are obtained in a simple manner by catalytic hydrogenation of the corresponding amines, for example

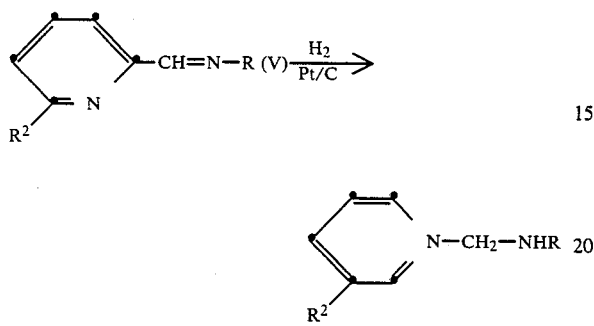

The pyridinaldimines of the formula V are known or can be obtained in a manner known per se by reacting unsubstituted or methyl-substituted 2-pyridinealdehyde with an amine $RNH_2$. Advantageously, pure stereoisomers of the amines $RNH_2$ are used, so that pure stereoisomers of the formula V are obtained. However, it is also possible to use racemates and subsequently resolve the resulting racemates of the formula V by well established methods.

Stereoisomers of the amines $RNH_2$ are known, and some of them are commercially available or can be prepared by known processes. Examples of such amines are: (R)-2-aminobutane, (R)-1-phenylethylamine, (S)-1-phenylethylamine, (R)-1-(α-naphthylethyl)-amine, (S)-2-amino-3-phenylpropane, (R)-1,2-diphenylethylamine, (S)-alaninol, (S)-phenylalaninol, (4S,5S)-5-amino-2,2-dimethyl-4-phenyl-1,3-dioxane, (S)-2-amino-1-methoxy-3-phenyl-propane, (R)-bornylamine, (R)-3-aminomethylpinane, (+)-dehydroabietylamine, (2R,4S,5S)-(+)-5-amino-2,4-diphenyl-1,3-dioxane [Chem. Ber. 113, pages 710–721 (1980)], (1S,2R)-(−)-2-methylcyclohexylamine [Chem. Ber. 117, pages 2076–2098 (1984)] and (1S,2S)-(+)-2-phenylcyclohexylamine [Chem. Ber. 117, pages 2076–2098 (1984)].

Optically active secondary amines of the formula IV, in which A is a radical of the formula IIa and $R^1$ and $R'$ are H, can likewise be obtained from the imines of the formula V by catalytic hydrogenation with, for example, $PtO_2$ as a catalyst.

Optically active secondary amines of the formula IV, in which A is a radical of the formula II, IIa or IIb and $R^1$ and $R'$ are H, can be prepared by the following process ($Z'$ is $-COOCH_2C_6H_5$ and * represents predominantly S or predominantly R configuration, the radical R in the amine $RNH_2$ containing no chiral C atom or at least one chiral C atom):

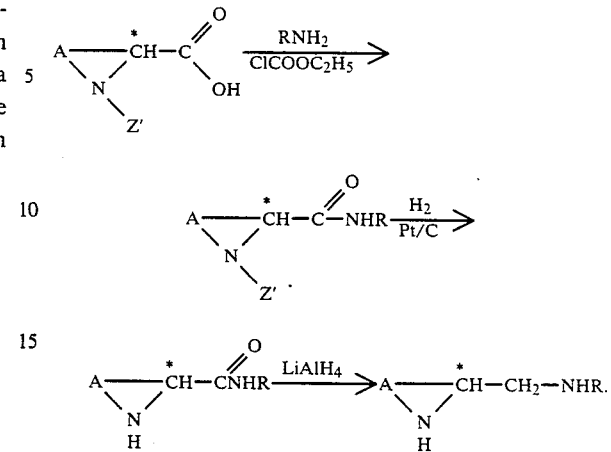

2-piperidine-, 2-pyrrolidine- and 2-indolinecarboxylic acid and their stereoisomers are known. Examples of suitable amines $R-NH_2$ are aniline, 1-amino-3-methylbenzene, 1-amino-2,6-dimethylbenzene, α-naphthylamine, (R)-1-phenylethylamine, (S)-1-phenylethylamine and (R)-1,2-diphenylethylamine.

The invention further relates to the use of the iridium complexes according to the invention as enantioselective homogeneous catalysts, in particular for the transfer hydrogenation of prochiral ketones with secondary alcohols. A particularly suitable secondary alcohol is isopropanol. The reaction is advantageously carried out in the absence of oxygen at elevated temperature, for example 40°–120° C. The secondary alcohol used is advantageously employed as the solvent. The amount of catalyst is preferably $10^{-2}$ to $10^{-5}$ mol/l, relative to the reaction volume. The reaction is preferably carried out in the presence of a base, in particular NaOH.

The Examples which follow illustrate the invention in more detail. The enantiomeric excess (ee) is determined according to Mosher [J. Org. Chem. 34, page 2543 (1969)].

EXAMPLES 1–9

0.469 g (1.0 mmol) of bis-(acetonitrile)-(cycloocta-1,5-diene)iridium tetrafluoroborate is dissolved in 15 ml of dichlormethane under argon protective gas. A solution of 5 ml of dichloromethane and 1.0 mmol of the N-substituted 2-(aminomethyl)-6-methylpyridine(N,N ligand) is added dropwise at room temperature and while stirring. After 1 hour, the reaction mixture is evaporated down to about one third of its volume, under about 600 Pa. If the product does not crystallize spontaneously, 60 ml of diethyl ether are added, the product being obtained as a solid precipitate in the course of 3 hours. The finely pulverulent product is filtered off under suction under argon, washed three times with diethyl ether and dried for about 16 hours under 0.1 Pa. The yields are 80% of theory. The colour and the elemental analysis of the complexes obtained are listed in Table 1.

TABLE 1

N,N = [pyridine-imine ligand with CH₃ and CH₂—A substituents]

| Example no. | Complex | A (absolute configuration) | Colour | Elemental analysis [% by weight] |
|---|---|---|---|---|
| 1 | [Ir(N,N)(COD)]BF₄ | —NH—CH(C₆H₅)(C₆H₅) (R) (diphenylmethyl-amino) | yellow | Found: C 49.5; H 5.02; N 4.10; Ir 27.5<br>Calc.: C 50.51; H 4.97; N 4.06; Ir 27.87 |
| 2 | " | —NH—CH(CH₃)(C₆H₅) (S) | orange | Found: C 44.23; H 5.27; N 4.37; Ir 28.5<br>Calc.: C 44.38; H 5.02; N 4.50; Ir 30.87 |
| 3 | " | —NH—CH(CH₃)(naphthyl) (R) | orange red | Found: C 46.33; H 4.96; N 4.01; Ir 27.2<br>Calc.: C 46.35; H 5.19; N 4.00; Ir 27.47 |
| 4 | " | —NH—CH(Ph)—CH(O—C(CH₃)₂—O) (4S, 5S) | dark yellow | Found: C 43.02; H 4.89; N 3.76; Ir 25.4<br>Calc.: C 43.03; H 5.62; N 3.72; Ir 25.5 |
| 5 | [Ir(N,N)(COD)]BF₄ | —NH—C(CH₃)H—(C₆H₅) (S) | yellow | Found: C 44.56; H 5.11; N 4.64; Ir 28.7<br>Calc.: C 44.45; H 5.37; N 4.15; Ir 28.45 |
| 6 | " | —NH—(menthyl) (1R) | pale yellow | Found: C 44.73; H 5.89; N 4.55; Ir 27.7<br>Calc.: C 44.05; H 6.21; N 4.11; Ir 28.2 |
| 7 | " | —NH—(trimethylcyclohexyl) (1S, 2S, 3S, 5R) | pale beige | Found: C 46.11; H 6.01; N 4.32<br>Calc.: C 46.08; H 6.25; N 4.13 |

TABLE 1-continued

N,N = [pyridine with CH₃ and CH₂—A substituents]

| Example no. | Complex | A (absolute configuration) | Colour | Elemental analysis [% by weight] |
|---|---|---|---|---|
| 8 | [Ir(N,N)(COD)]BF₄ | —NH— [phenyl-CH(O-)(O-)C(H)(isopropyl-phenyl)] (2R, 4S, 5S) | yellowish green | Found: C 48.15; H 4.98; N 3.55; Ir 24.9 Calc.: C 48.64; H 4.88; N 3.66; Ir 25.1 |
| 9 | " | —NH— [cyclohexyl with CH₃] (1S, 2R) | yellow | Found: C 42.20; H 5.56; N 4.52; Ir 29.6 Calc.: C 42.38; H 5.82; N 4.44; Ir 30.82 |

COD is cycloocta-1,5-diene

EXAMPLES 10–19

The N-substituted 2-(aminomethyl)pyridines described in detail in Table 2 are reacted with bis-(acetonitrile)(cycloocta-1,5-diene)iridium tetrafluoroborate analogously to Examples 1–9. After analogous working up, the complexes listed in Table 2 are obtained.

TABLE 2

N,N = [pyridine with CH₂A substituent]

| Example no. | Complex | A (absolute configuration) | Colour | Elemental analysis [% by weight] |
|---|---|---|---|---|
| 10 | [Ir(N,N)(COD)]BF₄ | —NH— [bicyclic with three CH₃ groups] (1R) | yellowish beige | Found: C 44.65; H 5.85; N 4.29; Ir 28.5 Calc.: C 44.38; H 5.90; N 4.31; Ir 29.5 |
| 11 | " | —NH— [phenyl-CH(O-)(O-)C(CH₃)₂] (4S, 5S) | yellowish beige | Found: C 49.16; H 4.89; N 4.10; Ir 26.2; F 10.27 Calc.: C 49.18; H 4.54; N 3.82; Ir 26.24; F 10.37 |
| 12 | " | —NH— [phenyl-CH(O-)(O-)C(H)(isopropyl-phenyl)] (2R, 4S, 5S) | yellowish orange | Found: C 45.67; H 4.66; N 4.02; Ir 26.0 Calc.: C 45.62; H 4.86; N 4.09; Ir 28.08 |

TABLE 2-continued $$N,N = \text{pyridyl-CH}_2A$$

| Example no. | Complex | A (absolute configuration) | Colour | Elemental analysis [% by weight] |
|---|---|---|---|---|
| 13 | " | 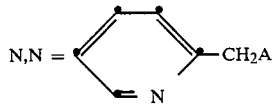 —NH— cyclohexyl-phenyl (1S, 2S) | yellow | Found: C 45.92; H 5.37; N 4.37<br>Calc.: C 45.79; H 5.44; N 4.45 |
| 14 | [Ir(N,N)(COD)]BF$_4$ | 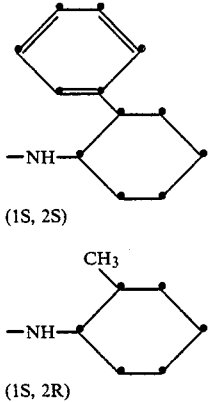 —NH—CH(CH$_3$)-cyclohexyl (1S, 2R) | orange | Found: C 42.1; H 5.5; N 4.8; Ir 31.4<br>Calc.: C 41.45; H 5.47; N 4.6; Ir 31.59 |
| 15 | " | —NH—CH(CH$_3$)$_2$ (R) | beige | Found: C 37.92; H 5.23; N 4.73; Ir 30.6<br>Calc.: C 37.94; H 5.70; N 4.66; Ir 31.9 |
| 16 | " | 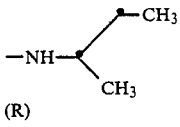 —NH—CH(phenyl)(naphthyl?) (R) | orange | Found: C 49.24; H 4.72; N 4.26; Ir 28.2<br>Calc: C 49.78; H 4.77; N 4.15; Ir 28.45 |
| 17 | " | 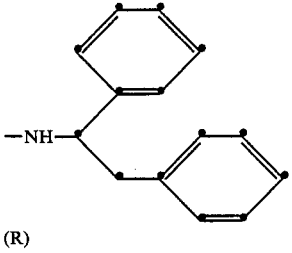 —NH—CH(CH$_3$)-cyclohexenyl (S) | yellowish orange | Found: C 44.61; H 4.78; N 4.47; Ir 30.1<br>Calc.: C 45.03; H 4.93; N 4.57; Ir 3.13 |
| 18 | [Ir(N,N)(COD)]BF$_4$ | 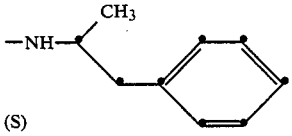 —NH—CH(CH$_3$)-phenyl (R) | orange | Found: C 43.66; H 4.88; N 4.52; Ir 30.5<br>Calc.: C 43.43; H 4.80; N 4.60; Ir 31.5 |
| 19 | " | 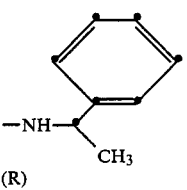 —NH—trimethylcyclohexyl (1S, 2S, 3S, 5R) | orange | Found: C 45.40; H 5.97; N 4.16; Ir 29.1<br>Calc.: C 45.25; H 6.08; N 4.22; Ir 29.0 |

EXAMPLES 20–26

The N-substituted 2-(aminomethyl)-piperidines described in detail in Table 3 are reacted with bis-(acetonitrile)(cycloocta-1,5-diene)iridium tetrafluoroborate analogously to Examples 1–9. After analogous working up, the complexes listed in Table 3 are obtained.

EXAMPLES 27–30

The N-substituted 2-(aminomethyl)-pyrrolidines listed in Table 4 are reacted with bis-(acetonitrile)(cycloocta-1,5-diene)iridium tetrafluoroborate analogously to Examples 1–9. After analogous working up, the complexes listed in Table 4 are obtained.

EXAMPLES 31-33

The N,N ligands listed in Table 5 are reacted with bis-(acetonitrile)(cycloocta-1,5-diene)iridium tetrafluoroborate analogously to Examples 1-9. After analogous working up, the complexes listed in Table 5 are obtained.

TABLE 3

N,N = (pyridyl-CH(*)-CH₂-A, NH)

| Example no. | Complex | A (absolute configuration)[1] | | Colour | Elemental analysis [% by weight] |
|---|---|---|---|---|---|
| 20 | [Ir(N,N)(COD)]BF₄ | —NH—(phenyl) | (S) | green | Found: C 40.64; H 5.35; N 4.82; Ir 31.9<br>Calc.: C 40.34; H 5.42; N 4.70; Ir 32.28 |
| 21 | " | —NH—CH(phenyl)₂ | (R,R) | beige | Found: C 46.80; H 5.57; N 3.98; Ir 26.6<br>Calc.: C 46.86; H 5.90; N 3.90; Ir 26.8 |
| 22 | " | —NH—CH(CH₃)(phenyl) | (R,R) | pale beige | Found: C 42.82; H 5.53; N 4.56; Ir 31.1<br>Calc: C 42.38; H 5.82; N 4.49; Ir 30.82 |
| 23 | " | —NH—CH(CH₃)(phenyl) | (S,R) | yellow | Found: C 41.56; H 5.64; N 4.43; F 11.74<br>Calc.: C 41.19; H 5.97; N 4.37; F 11.85 |
| 24 | [Ir(N,N)(COD)]BF₄ | —NH—CH(CH₃)(phenyl)<br>(diastereomer mixture: R,R: S,R = 43:57) | (R,S) | greenish yellow | Found: C 42.68; H 5.43; N 4.64; Ir 30.1<br>Calc.: C 42.38; H 5.82; N 4.49; Ir 30.82 |
| 25 | " | —NH—CH(CH₃)(phenyl)<br>(diastereomer mixture: R,S: S,S = 42:58) | | beige | Found: C 43.41; H 5.67; N 4.63; Ir 30.1<br>Calc.: C 43.64; H 5.66; N 4.63; Ir 31.74 |

TABLE 3-continued $$N,N = \underset{NH}{\overset{\phantom{x}}{\bigcirc}}*-CH_2-A$$

| Example no. | Complex | A (absolute configuration)[1] | Colour | Elemental analysis [% by weight] |
|---|---|---|---|---|
| 26 | [Ir(N,N)(COD)]BF$_4$ | 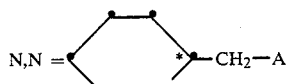<br>(diastereomer mixture:<br>S,4S,5S R,4S,5S ~ 1:1) | beige orange | Found: C 46.41; H 5.34; N 3.53; Ir 24.4<br>Calc.: C 46.43; H 5.72; N 3.61; Ir 24.78 |

(1) The first symbol (R or S) relates to the 2-position in the piperdine ring

TABLE 4

$$N,N = \underset{\underset{H}{N}}{\overset{\phantom{x}}{\bigcirc}}*-CH_2-A$$

| Example no. | Complex | A (absolute configuration)[1] | Colour | Elemental analysis [% by weight] |
|---|---|---|---|---|
| 27 | [Ir(N,N)(COD)]BF$_4$ | 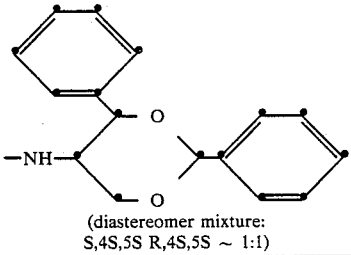 (S) | yellow | Found: C 39.46; H 5.14; N 4.79; Ir 33.1<br>Calc.: C 39.25; H 5.20; N 4.82; Ir 33.05 |
| 28 | " | 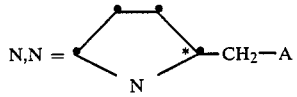 (S) | lemon yellow | Found: C 42.52; H 5.50; N 4.66; Ir 32.2<br>Calc.: C 42.64; H 5.45; N 4.74; Ir 32.50 |
| 29 | " | 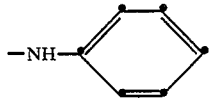 (S,S) | pale yellow | Found: C 40.84; H 5.42; N 4.75; Ir 31.5<br>Calc.: C 41.38; H 5.62; N 4.60; Ir 31.53 |
| 30 | " | 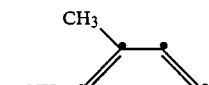<br>(S, 2R, 4S, 5S) | yellow | Found: C 46.36; H 5.11; N 3.90; Ir 25.2<br>Calc.: C 46.84; H 5.42; N 3.77; Ir 25.85 |

| Example no. | Complex | N,N—Ligand | Colour | Elemental analysis |
|---|---|---|---|---|
| 31 | [Ir(N,N)(COD)]BF$_4$ | 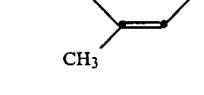<br>diastereomer mixture | brown | Found: C 49.13; H 5.96; N 3.94; Ir 25.8<br>Calc.: C 48.81; H 5.93; N 3.93; Ir 26.0 |

TABLE 4-continued

| 32 | " | 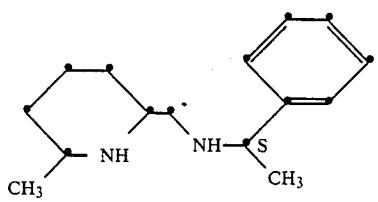 | yellow | Found: C 43.80; H 5.65; N 4.51; Ir 29.4 |
|---|---|---|---|---|
|  |  |  |  | Calc.: C 43.54; H 5.56; N 4.42; Ir 30.29 |
|  |  | diastereomer mixture |  |  |
| 33 | " | 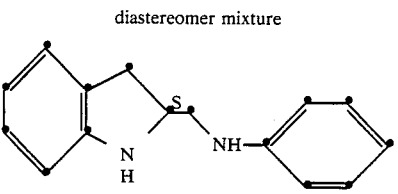 | greenish yellow | Found: C 44.27; H 4.90; N 4.44; Ir 29.7 |
|  |  |  |  | Calc.: C 43.88; H 4.80; N 4.45; Ir 30.53 |

(1) The first symbol (R or S) relates to the 2-position of the pyrrolidine ring

EXAMPLE 34

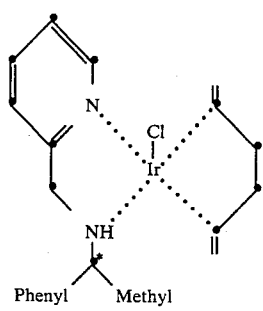

0.337 g (0.376 mmol) of di-μ-chlorotetrakis(cyclooctene)diiridium(I) is dissolved in 26 ml of benzene under argon protective gas. 2.6 ml of 1,5-hexadiene are added dropwise at 10° C. The mixture is stirred for 1 hour, after which a solution of the diamine in 2 ml of benzene is added dropwise. The reaction mixture is stirred for 1 hour at room temperature and then filtered over Celite. The product is precipitated as a beige powder when 120 ml of hexane are added. It is filtered off, washed several times with hexane and dried for 18 hours under 0.1 Pa.

Colour: beige
Microanaylsis (formula:

| $C_{20}H_{26}N_2ClIr$: | C | H | N | Cl |
|---|---|---|---|---|
| Calculated | 46.01 | 5.02 | 5.37 | 6.79 |
| Found | 40.61 | 4.74 | 4.1 | 7.58 |

The product contains about 20% of di-μ-chlorotetrakis(cyclooctene)diiridium(I).

EXAMPLE 35 (USE EXAMPLE)

6.42 mg of the complex prepared according to Example 2 are dissolved in 39.5 ml of isopropanol in the absence of oxygen (argon atmosphere). After the solution has been stirred for 1 hour at 60° C., 0.42 ml of 0.1N sodium hydroxide solution is added. Stirring is continued for a further hour at 60° C., and a solution of 39.5 ml of isopropanol and 1.55 g of butyrophenone is then added in the absence of oxygen. The molar ratio of substrate to catalyst is thus [s]/[cat.]=1000, and the catalyst concentration is $1.33.10^{-4}$ mol/l.

After 3 hours at 60° C., the yield of 1-phenyl-1-butanol is determined as 90.9% of theory by gas chromatography (OV 101, 120° C., isothermal).

To determine the enantiomer content according to Mosher, a sample of the reaction mixture (about 0.5 ml) is substantially freed from the solvent, and 50 μl of optically pure α-methoxy-α-trifluoromethylphenylacetyl chloride and 0.25 ml of dry pyridine are added at 0° C. After 15 minutes, the mixture is heated to 70° C. for 30 minutes and cooled, after which 3 ml of 10% citric acid solution are added and the diastereomeric esters are extracted with ether.

An enantiomeric excess ee of (S)-1-phenylbutanol of 54.2% is determined by gas chromatography (capillary column CW 20, 190° C.).

EXAMPLE 36 (USE EXAMPLE)

The complex according to Example 2 is used for the catalytic, enantioselective transfer hydrogenation of isobutyrophenone, analogously to Example 35.

After 1 hour 45 minutes, the yield of 1-phenyl-2-methylpropanol is 95.3%, and the enantiomeric excess ee is 57.3% of (S).

EXAMPLE 37 (USE EXAMPLE)

The complex according to Example 1 is used for the catalytic, enantioselective transfer hydrogenation of butyrophenone, analogously to Example 35.

After 12 hours 45 minutes, the yield of 1-phenyl-butanol is 90.4%, and the enantiomeric excess ee is 60.4% of (R).

EXAMPLE 38 (USE EXAMPLE)

The complex according to Example 12 is used for the catalytic, enantioselective transfer hydrogenation of butyrophenone, similarly to Example 35. However, the concentration conditions [S]/[cat.]=100 and [cat.]=$2.10^{-3}$ mol/l are chosen.

After 18 hours, the yield is 78.8% of 1-phenylbutanol, and the enantiomeric excess ee is 55.3% of (S).

EXAMPLE 39 (USE EXAMPLE)

The complex according to Example 23 is used for the catalytic, enantioselective transfer hydrogenation of butyrophenone, similarly to Example 35. However, the concentration conditions [S]/[cat.]=1000 and [cat.]=$1.33.10^{-4}$ mol/l are chosen.

After 20 hours, the yield is 88.8% of 1-phenylbutanol, and the enantiomeric excess ee is 60.1% of (R).

EXAMPLE 40 (USE EXAMPLE)

The complex according to Example 25 is used for the catalytic, enantioselective transfer hydrogenation of butyrophenone, similarly to Example 35. However, the concentration conditions [S]/[cat.]=1000 and [cat.]=1.33.10$^{-4}$ mol/l are chosen.

After 20 hours, the yield is 45.3% of 1-phenylbutanol, and the enantiomeric excess ee is 54.1% of (S).

EXAMPLE 41 (USE EXAMPLE)

The complex according to Example 20 is used for the catalytic, enantioselective transfer hydrogenation of butyrophenone, similarly to Example 35. However, the concentration conditions [S]/[cat.]=1000 and [cat.]=1.33.10$^{-1}$ mol/l are chosen.

After 20 hours 30 minutes, the yield is 31.2% of 1-phenylbutanol, and the enantiomeric excess ee is 49.3% of (R).

EXAMPLE 42 (USE EXAMPLE)

The complex according to Example 27 is used for the catalytic, enantioselective transfer hydrogenation of butyrophenone, analogously to Example 35.

After 20 hours, the yield is 39.0% of 1-phenylbutanol, and the enantiomeric excess ee is 29.2% of (R).

EXAMPLE 43 (USE EXAMPLE)

The complex according to Example 32 is used for the catalytic, enantioselective transfer hydrogenation of butyrophenone, similarly to Example 35. However, the concentration conditions [S]/[cat.]=1000 and [cat.]=1.33.10$^{-4}$ mol/l are chosen.

After 2 hours, the yield is 95.0% of 1-phenylbutanol, and the enantiomeric excess ee is 60.4% of (S).

What is claimed is:

1. An optically active iridium complex of the formula I and a mixture of the diastereomers

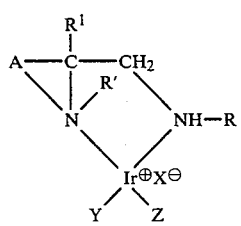

in which R$^1$ and R' are H and A is a radical of the formula II, IIa or IIb

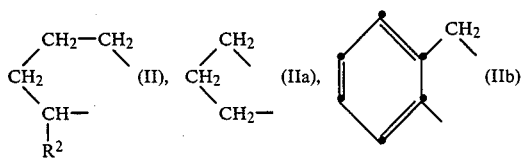

or R$^1$ and R' represent a bond and A is a radical of the formula IIc

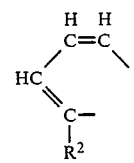

in which R$^2$ is —H or —CH$_3$, X$^\ominus$ is an anion of an inorganic or organic acid, Y and Z are each ethylene, or Y and Z together represent an open-chain or cyclic diene having 6-10 C atoms, whose double bonds are separated by one or two C atoms; and R is a radical of the formula III

in which R$^3$, R$^4$ and R$^5$ differ from one another when they do not contain at least 1 chiral C atom, and are a hydrogen atom, C$_1$-C$_4$-alkyl, C$_1$-C$_4$-alkoxy, cycloalkyl having 5 to 7 ring C atoms which is unsubstituted or substituted by C$_1$-C$_4$-alkyl or phenyl, cycloalkylalkyl which is unsubstituted or substituted by C$_1$-C$_4$-alkyl or phenyl and has 5 to 7 ring C atoms and 1 or 2 C atoms in the alkylene group, phenyl, naphthyl, benzyl or β-phenylethyl; or R$^4$ and R$^5$ together are C$_1$-C$_4$-alkyl-substituted or phenyl-substituted linear C$_4$- or C$_5$-alkylene, C$_4$- or C$_5$-oxaalkylene or C$_5$-dioxaalkylene having one, two or three chiral C atoms, or R$^3$ and R$^5$ are each H and R$^4$ corresponds to the formula

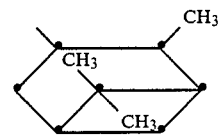

or the group —CR$^3$R$^4$R$^5$ corresponds to the formula

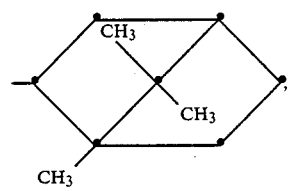

or A is a radical of the formula II, IIa or IIb and R is phenyl, naphthyl, 2-methylphen-1-yl or 2,6-dimethylphen-1-yl.

2. An iridium complex of the formula I according to claim 1, wherein X$^\ominus$ is BF$_4^\ominus$, ClO$_4^\ominus$, CF$_3$SO$_3^\ominus$ or PF$_6^\ominus$.

3. An iridium complex of the formula I according to claim 1, wherein Y and Z together are 1,5-cyclooctadiene, norbornadiene or 1,5-hexadiene.

4. An iridium complex of the formula I according to claim 1, wherein R is a radical of the formula III

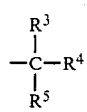 (III)

in which $R^3$, $R^4$ and $R^5$ differ from one another when they do not contain at least 1 chiral C atom, and are a hydrogen atom, $C_1$–$C_4$-alkyl, $C_1$–$C_4$-alkoxy, cycloalkyl having 5 to 7 ring C atoms which is unsubstituted or substituted by $C_1$–$C_4$-alkyl or phenyl, cycloalkylalkyl which is unsubstituted or substituted by $C_1$–$C_4$-alkyl or phenyl and has 5 to 7 ring C atoms and 1 or 2 C atoms in the alkylene group, phenyl, naphthyl, benzyl or β-phenylethyl; or $R^4$ and $R^5$ together are $C_1$–$C_4$-alkyl-substituted or phenyl-substituted linear $C_4$- or $C_5$-alkylene, $C_4$- or $C_5$-oxaalkylene or $C_5$-dioxaalkylene having one, two or three chiral C atoms; or $R^3$ and $R^5$ are each H and $R^4$ corresponds to the formula

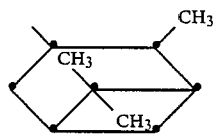

or the group —$CR^3R^4R^5$ correspond to the formula

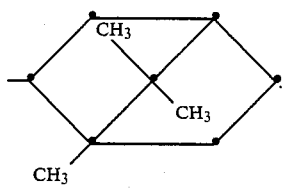

5. An iridium complex of the formula I according to claim 4, wherein $R^3$ in formula III is H.

6. An iridium complex of the formula I according to claim 4, wherein, in formula III, $R^3$ is H, $R^4$ is $C_1$–$C_4$-alkyl, $C_1$–$C_4$-alkoxy or phenyl and $R^5$ is phenyl, benzyl or naphthyl, and $R^3$ and $R^4$ are not both phenyl; or $R^3$ and $R^5$ are each H and $R^4$ corresponds to the formula

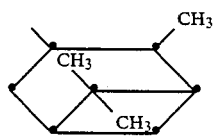

or the group —$CR^3R^4R^5$ corresponds to the formula

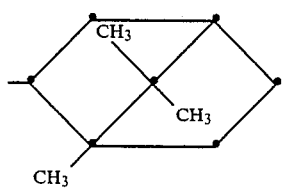

or $R^3$ is H and $R^4$ and $R^5$ together are pentamethylene which is substituted in the 2-position by $C_1$–$C_4$-alkyl, or are 2,4-dioxapentylene which is substituted in the 1- and/or 3-position by $C_1$–$C_4$-alkyl or phenyl.

7. An iridium complex of the formula I according to claim 4, wherein the radical of the formula II corresponds to the radicals

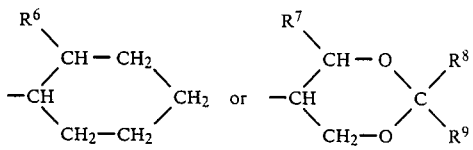

in which $R^6$ is methyl or phenyl, $R^7$ is methyl or phenyl and $R^8$ and $R^9$ are methyl, or $R^8$ is H and $R^9$ is phenyl.

8. An iridium complex of the formula I according to claim 1, wherein $R^1$ and $R'$ are a bond and A is a radical of the formula IIc, in which $R^2$ is methyl and R corresponds to the radicals

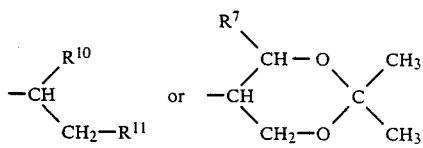

in which $R^7$ is phenyl, $R^{10}$ is phenyl or naphthyl and $R^{11}$ is H, or $R^{10}$ and $R^{11}$ are phenyl.

9. An iridium complex of the formula I according to claim 1, wherein $R^1$ and $R'$ are a bond and A is a radical of the formula IIc, in which $R^2$ is H and R is 2-methylcyclohex-1-yl, 2-phenylcyclohex-1-yl

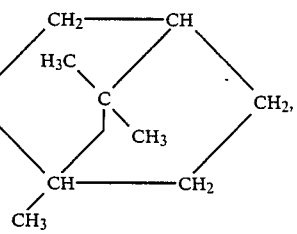

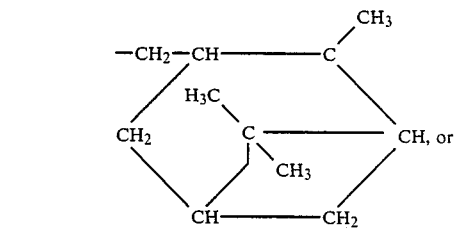

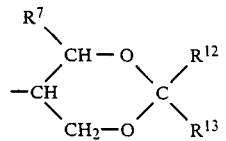

in which $R^7$ is phenyl and $R^{12}$ and $R^{13}$ are —$CH_3$, or $R^{12}$ is H and $R^{13}$ is phenyl.

10. An iridium complex of the formula I according to claim 1, wherein $R^1$ and $R'$ are H and A is a radical of the formula II and R is a radical

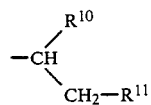

in which $R^{10}$ and $R^{11}$ are phenyl, or $R^{10}$ is phenyl or naphthyl and $R^{11}$ is H, or $R^{10}$ is methyl and $R^{11}$ is phenyl.

11. An iridium complex of the formula I according to claim 1, wherein $R^1$ and $R'$ are H and A is a radical of the formula IIa, and R is phenyl, 2-methylphen-1-yl or 2,6-dimethylphen-1-yl.

12. An iridium complex of the formula I according to claim 1, wherein $X^\ominus$ is $BF_4^\ominus$ and Y and Z together are 1,5-cyclooctadiene.

* * * * *